United States Patent [19]

Hoess et al.

[11] Patent Number: 5,519,142

[45] Date of Patent: May 21, 1996

[54] HOMOBIDENTAL, TRIFUNCTIONAL LINKERS, METHOD FOR THEIR PREPARATION AND USE IN IMMUNOLOGICALLY ACTIVE CONJUGATES

[75] Inventors: Eva Hoess, Starnberg; Erasmus Huber, Finning; Christine Markert-Hahn, Seeshaupt; Beatus Ofenloch-Haehnle, Wielenbach, all of Germany

[73] Assignee: Boehringer Mannheim GmbH, Mannheim, Germany

[21] Appl. No.: 219,469

[22] Filed: Mar. 29, 1994

[30] Foreign Application Priority Data

Mar. 29, 1993 [DE] Germany .................. 43 10 141.0

[51] Int. Cl.⁶ .................. C07D 401/14; C07D 403/14
[52] U.S. Cl. .................. 548/251; 548/314.7; 546/281
[58] Field of Search .................. 548/571, 314.7; 546/281

[56] References Cited

U.S. PATENT DOCUMENTS

| | | | |
|---|---|---|---|
| 5,082,930 | 1/1992 | Nicolotti et al. | 530/402 |
| 5,083,930 | 1/1992 | Barron | 439/101 |
| 5,091,542 | 2/1992 | Ahlem et al. | 548/521 |
| 5,168,057 | 12/1992 | Oh et al. | 435/174 |
| 5,244,785 | 9/1983 | Loor et al. | 435/5 |

FOREIGN PATENT DOCUMENTS

| | | |
|---|---|---|
| 0247866 | 5/1987 | European Pat. Off. . |
| 0310361 | 9/1988 | European Pat. Off. . |
| 0446071 | 3/1991 | European Pat. Off. . |
| 92/22583 | 12/1992 | WIPO . |

OTHER PUBLICATIONS

Derwent Abstract 85-226374 of JP60146154 Pub. (1985) under A04 85-226374.

*Primary Examiner*—David B. Springer
*Attorney, Agent, or Firm*—Nikaido, Marmelstein, Murray & Oram

[57] ABSTRACT

Compound of the general formula

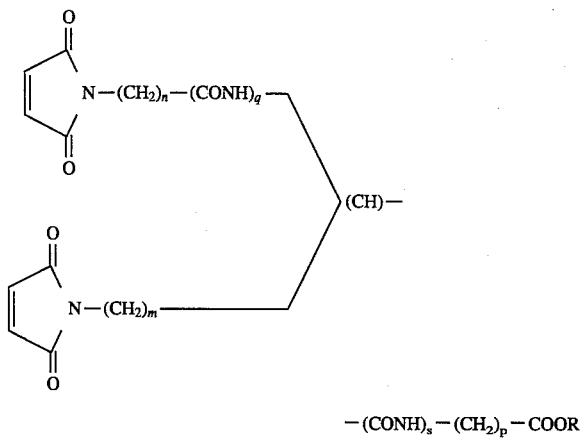

wherein R is an ester-activating group, m and n are identical or different and 0–6, p= 0, 2–4, and q and s= 1, p=0 if s=0 and p= 2–4 if s=1. The compound is novel and suitable for the reproducible coupling of immunological substances at a high yield.

8 Claims, No Drawings

HOMOBIDENTAL, TRIFUNCTIONAL LINKERS, METHOD FOR THEIR PREPARATION AND USE IN IMMUNOLOGICALLY ACTIVE CONJUGATES

The invention addresses homobidental, trifunctional linkers, their preparation and use for the preparation of immunologically active substances (e.g. immunogens, labelled antibody conjugates) and for coupling immunologically active substances to one another or to carrier substances, such as proteins or other polymers.

Immunologically active substances are coupled to carrier proteins or labels which can be detected in an immunoassay via bifunctional linkers or, if more than two molecules are to be linked or if two binding sites are required to bind a molecule, via trifunctional linkers. U.S. Pat. No. 5,082,930 describes a trifunctional linker to couple antibodies to radioactive metal ions. In this specification, an antibody is covalently linked to a functional group of the linker while a radioactive metal ion is bound in form of a chelate complex via the two remaining functional groups of the linker.

U.S. Pat. No. 5,168,057 discloses trifunctional conjugates in which at least two of the linker functions are bound to small molecules. The length and chemical structure of the three linker arms are such that an immunological binding of several antibodies to this small molecule is sterically hindered. This hindrance is the basis for an immunoassay.

U.S. Pat. No. 5,091,542 also discloses trifunctional linkers where the three coupling groups are identical, each being a maleinimido group. With these homotrifunctional linkers it is possible to link three antibodies or antibody fragments or even two antibodies to each other. In the latter case, however, one of the antibodies is bound to the trifunctional linker via two of its thiol groups.

The reaction of the proteins with such homotrifunctional linkers, however, induces uncontrollable cross-linking since the individual reaction partners have to be coupled to one another in one single reaction step.

It was, hence, an object of the present invention to provide homobidental trifunctional linkers to couple thiol group-containing compounds with proteins, polymers, and haptens in a reproducible manner and at a high yield. This object is accomplished by a compound of the general formula

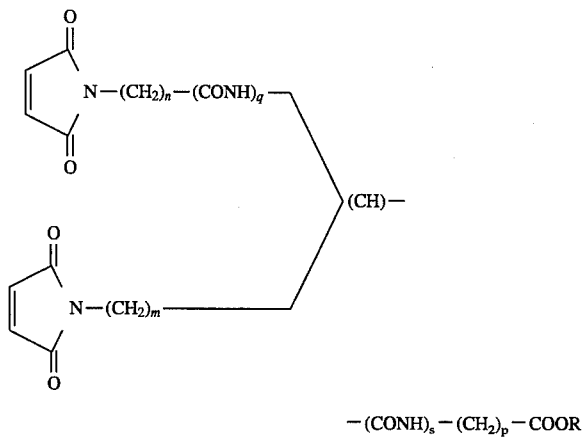

wherein R is an ester-activating group, m and n are equal or different and 0–6, q and s are 0 or 1, p= 0 if s=0, and p=2–4 if s=1.

The compounds in accordance with the invention are novel. They cannot be prepared in analogous methods.

Experience has shown that such compounds allow stable coupling between haptens, proteins, and/or polymers such as dextranes and the conjugates produced with the aid of the compounds in accordance with the invention are available at a high yield. The expert can determine the yield of the coupling according to common methods (e.g. by determining the number of SH groups in the conjugate according to G. L. Ellman, Arch. Biochem. Biophys. 74 (1958) 443–450, or P. W. Riddles, Anal. Biochem. 94 (1979) 75–81).

Preferred ester-activating groups R are N-hydroxyester groups (e.g. the hydroxysuccinimidyl group), imidazolides, pyridazolides, aminoalkyl carboxylic acids, or activated arylester groups (e.g. p-nitrophenylester). In the invention, n, m, p, q, and s can assume all given values. However, experience has shown that long-chain linkers are particularly suitable to couple large haptens.

Particularly preferred compounds are those wherein
a) R: hydroxysuccinimidyl, n=5, m=4, p=2 and q and s=1 and compounds wherein
b) R: hydroxysuccinimidyl, n and m=5, p=0, and p and s=0
c) R: hydroxysuccinimidyl, n and m=3, p=0, q and s=0
d) R: hydroxysuccinimidyl, n=5, m=4, p=0, q=1, s=0

The linkers in accordance with the invention are preferably used to couple immunologically active substances such as antibodies and antibody fragments with haptens, proteins, and dextrane.

Such coupling products can be advantageously used as immunogens as it is possible to couple twice the amount of haptens to one carrier protein. The immune responses are particularly pronounced if the immunogen used is sufficiently loaded with haptens.

Further, it is advantageous if the immunogen has an alkaline pI value (A. Muckerheide et al., J. Immunol. 138 (1987) 833; R. J. Apple et al., J. Immunol. 140 (1987) 3290; P. L. Domen, J. Immunol. 139 (1987) 3195). One possibility to increase the isoelectric point is the incorporation of additional amino groups in the carrier proteins (U.S. Pat. No. 5,162,219; A. Muckerheide et al., J. Immunol. 138 (1987), 2800; Pierce Supercarrier 77150). Activation via the maleinimido or mercapto groups is then carried out in a second step.

With the linkers in accordance with the invention, it is also possible to obtain a sufficiently high loading of the immunogens without derivatizing all amino groups of the protein. With the amounts of protein available during the reaction, it is possible to control the incorporation of linkers of the invention.

In immunoassays, the degree at which the conjugates are loaded with haptens has a decisive influence on the sensitivity of the assay, as is the case, for example, in the detection of high-molecular analytes according to the CEDIA principle (U.S. Pat. No. 5,244,785). Analytes with a low concentration can only be detected with highly loaded antibody-ED-conjugates (ED=β-galactosidase enzyme donor). The degree of loading is, however, restricted by the number of available ε-amino groups of the antibody or the antibody fragment. With the homobidental, trifunctional linkers, it is possible to double the incorporation without cross-linking the antibodies. This in turn increases the sensitivity of the assay.

It is, therefore, preferred to couple two β-galactosidase ED-subunits or two haptens via the two maleinimido groups of the linkers of the invention to an antibody or an antibody fragment or a dextrane which in turn is bound to the linker of the invention via the activated R group. In other preferred conjugates, two haptens are coupled to an ED-subunit via the two maleinimido groups of the linkers of the invention, while said ED-subunit is bound to a linker of the invention via the activated R group.

Methods of activating and coupling haptens, proteins, and antibodies are known to the expert. Preparation of maleinimide derivatives and their coupling to SH groups is described in O. Keller, Helvetica Chimica Acta 58 (1975) 531–541. Acidic amides can, for example, be prepared according to U.S. Pat. No. 4,442,029. The aminization of proteins can be accomplished in accordance with U.S. Pat. No. 5,162,219, for example.

The synthesis of linkers of the invention wherein q=0 and s=0, can be accomplished by a two-fold malonic ester synthesis with N-phtalimido alkyl halogenides (preferably bromide) and malonic diester (preferably malonic di-t-butylester). The result is a dialkyl malonic diester. After cleaving the malonic diester in an acidic milieu (preferably trifluoroacetic acid), decarboxylation (acid cleavage) occurs when the mixture is heated up. Subsequently, the amino groups can be released by treatment with hydrazin or by means of acidic hydrolysis. The two maleinimidyl residues are incorporated by treatment with alkoxy carbonyl maleinimide (preferably methoxy- or ethoxycarbonyl maleinimide (O. Keller, Ioc. cit.)). Further, the carboxyl group is activated according to methods that are known to the expert, for example, using dicyclohexylcarbodiimide (DCCI) and N-hydroxysuccinimide. An additional reaction of the activated esters with ω-aminocarboxylic acids (e.g. β-alanin, U-aminocaproic acid) and subsequent activation with DCCI and N-hydroxysuccinimide, for example, produces linkers in accordance with the invention wherein q=0 and s=1. The result is a linker in accordance with the invention which contains two maleinimidyl residues and one hydroxysuccinimide ester functional group as R. Other R residues can be incorporated by derivatizing the carboxyl group according to methods that are known to the experts.

Linkers in accordance with the invention where q and s=1 can be synthesized by reacting a diamino acid where one of the amino groups is protected by an acid-labile protective group (preferably t-butyloxycarbonyl) with alkoxycarbonyl maleinimides, preferably with methoxy- or ethoxycarbonyl maleinimide (). Keller, Ioc. cit.) Subsequently, the resulting compound is reacted with an amino acid at the free carboxyl group.

If an α-diaminocarboxylic acid is used, it is advantageous to link the molecule either with an ω-aminocarboxylic acid (preferably β-alanin) or with a corresponding amino-derivatized compound to be coupled such as hapten (preferably a biotin derivative). The coupling of the amino group to the free carboxyl group is achieved by use of coupling methods that are known to the expert (preferably with carbodiimides and N-hydroxysuccinimide).

After cleaving off the protective groups under acidic conditions (e.g. using trifluoroacetic acid or 2N hydrogen chloride in dioxane), the resulting compound is reacted with an carboxyl-activated alkyl carboxylic acid (preferably maleinimidohexanoxyl-N-hydroxysuccinimide). The free carboxyl groups are activated according to methods that are known to the expert, for example, using morpholinoethylisocyanide and N-hydroxysuccinimide.

The synthesis of linkers according to the invention where q=1 and s=0 can be carried out analogously starting with diamino acids with none of the amino groups being protected by a protective group in the first step.

The proteins with trifunctional linkers can be activated by means of a nucleophile substitution of the N-hydroxysuccinimide group of the linker by an ε-amino group of the lysine side chain of proteins in a slightly alkaline buffer. To achieve this, a 1–8-fold excess of linkers, referred to the amino groups of the proteins to be derivatized, is used. The N-hydroxysuccinimide and the excess linker formed during the reaction are separated by means of dialysis or gel chromatography.

Amino group-containing haptens can be reacted either in organic media, such as dioxane or DMF under the addition of triethylamine or in buffer mixtures, preferably potassium phosphate buffer, pH 7.5, with equimolar amounts of linkers according to the invention.

The protein content in the solution (to determine the yield of the reaction) can be determined with the "BCA protein assay test" by Pierce Chemicals (Cat. No. 23225) (P. K. Smith, Anal. Biochem. 150 (1985) 76–85).

The degree at which the proteins are loaded with maleinimido groups is preferably determined with "Eliroans reagent" (5,5'-dithio-bis-(2-nitrobenzoic acid)). For the conjugate synthesis, SH-activated haptens and maleinimido-activated proteins are reacted such that the SH-activated hapten is made to react with a protein having a maleinimido group in protective gas atmosphere (e.g. argon) in a potassium phosphate buffer in a slightly acidic environment. The hapten is bound to the protein resulting in the formation of a thioether binding. The amount of SH-active hapten to be used in the reaction depends on the number of maleinimido groups of the conjugate used consisting of protein and linker. A ratio of 2:1 of SH:maleinimido groups has proven well to obtain a complete reaction.

The following examples are intended to further illustrate the invention:

EXAMPLE 1

1.1 N-α-Boc-ε-maleinimido-α-aminohexanoic acid (α-Boc-ε-Mal-Lys)

200 ml saturated sodium hydrogen carbonate solution are added to 3.70 g (15 mmol) of α-t-butyloxylcarbonyl lysine, reacted with 2.54 g (15 mmol) N-ethoxycarbonyl-maleinimide and stirred for 30 min at 20° C. Subsequently, the reaction solution is diluted with 200 ml of water, adjusted to a pH of 1.8 using 2N hydrochloric acid, extracted twice with ethyl acetate using 200 ml each time, and dried over magnesium sulfate and the solvent is then removed by distilling in a vacuum produced by a water pump. The raw product is purified by means of open column chromatography (5×50 cm) over silica gel, eluent: ethyl acetate/methanol (v/v 4/1)/1% acetic acid. The product containing fractions are purified, the solvent is removed in a vacuum produced by a water pump and the residue is dried in a high vacuum over $CaCl_2$.

Yield: 3.8 g (11.58 mmol) 78% of theoretical

TLC: Silica gel (Merck 60), ethyl acetate/methanol (v/v 3/2)/1% acetic acid, detection with potassium permanganate $R_f$=0.83

$^1$H-NMR ($D_6$-DMSO/TMS): δ=1.35 (m, 15H, $^t$Bu u. 3 C $\underline{H}_2$); 3.35 (m, 2H, C$\underline{H}_2$-N); 3.66 (m, 1H, C$\underline{H}$-N); 6.18 (d, br, 1H, N$\underline{H}$, J= 7.2 Hz); 6.98 ppm (s, 2H, C$\underline{H}$= ).

1.2 N-α-Boc-ε-maleinimido-α-aminohexanoyl-β-alanin (α-Boc-ε-Mal-Lys-β-Ala)

676 mg (5.92 mmol) N-hydroxysuccinimide and 1.21 g (5.92 mmol) dicyclohexylcarbodiimide are added to 1.60 g (4.9 mmol) of the compound of example 1.1 in 200 ml of THF and stirred for 20° C. at 1 hour. 480 mg (5.4 mmol)

β-alanin are dissolved in 200 ml of 0.1M KPO$_4$ buffer, pH 8.5, and added dropwise to the reaction mixture. After 16 hours of stirring at 20° C., the organic solvent is removed by distilling in a vacuum produced by a water pump, the aqueous phase is diluted with 100 ml water, extracted twice with ethyl acetate using 250 ml each time, dried over magnesium sulfate and concentrated in a vacuum produced by a water pump. The residue is dried over a silica gel column (5×30 cm), the eluent is ethyl acetate/methanol (v/v 4/1)/1% acetic acid.

Yield: 1.1 7 g (2.96 mmol) 61% of theoretical

TLC: Silica gel (Merck 60), ethyl acetate/methanol (v/v 4/1)/1% glacial acetic acid, detection with potassium permanganate $R_f$=0.7

$^1$H-NMR (D$_6$-DMSO/TMS): δ=1.35 (m, 15H, $^t$Bu u. 3 C$\underline{H}_2$); 2.32 (t, 2H, C$\underline{H}_2$CO, I=6.9 Hz); 3.16–3.41 (m, 4H, C$\underline{H}$-N); 3.88 (m, 1H, C$\underline{H}$-N); 6.73 (d, 1H, N$\underline{H}$-COO, J=7.7 Hz); 6.98 (s, 2H, C$\underline{H}$=); 7.78 ppm (t, 1H, N$\underline{H}$-CO, J=5.4 Hz).

1.3 ε-Maleinimido-α-aminohexanoyl-β-alanin (ε-Mal-Lys-β-Ala)

15 ml trifluoro acetic acid are added to 710 mg (1.8 mmol) of the compound of the example 1.2 at 0° C. under stirring and then slowly heated up to 20° C. After 30 min, the solution is diluted with 15 ml of ethyl acetate and stirring is continued for another 15 min at 20° C. The solvent is then removed by distilling in a vacuum produced by a water pump and the residue is lyophilized from dioxane/water (v/v 1/1).

Yield: 430 mg (1.5 mmol) 81% of theoretical

TLC: Silica gel (Merck 60), ethyl acetate/methanol (v/v 1/4)/1% glacial acetic acid, detection with ninhydrin $R_f$=0.33

$^1$H-NMR (D$_6$-DMSO/TMS): δ=1.35–1.64 (m, 6H, 3 C$\underline{H}_2$); 2.41 (t, 2H, C$_2$-CO, J=6.6 Hz); 3.37 (m, 4H, 2 C$\underline{H}_2$-N); 3.68 (m, 1H, C$\underline{H}$-N); 7.00 (s, 2H, C$\underline{H}$=); 8.53 ppm (t, 1H, N$\underline{H}$-CO, I=6.0 Hz).

1.4 N-α-(6-maleinimidohexanoyl)-ε-maleinimido-α-aminohexanoyl-β-alanin (ε-MHS-ε-Mal-Lys-β-Ala)

A solution of 462 mg (1.5 mmol) maleinimidohexanoic acid-N-hydroxysuccinimide ester (MHS) in 10 ml THF is added in dropwise to a solution consisting of 400 mg (1.35 mmol) of the compound of the example 3.3 in 10 ml of 0.1M KPO$_4$ buffer pH 7.5 under stirring. The pH is adjusted to a value of 7.5 using 1N sodium hydroxide solution. After 16 hours of stirring at 20° C., the organic solvent is removed by distilling in a vacuum produced by a water pump, the residue is diluted with 10 ml of water and adjusted to a pH of 3.0 using 1N hydrochloric acid and extracted three times with ethyl acetate using 30 ml each time. The product is then converted into the organic phase. The phase is then dried with magnesium sulfate and concentrated in a vacuum produced by a water pump. The residue is purified by means of open column chromatography over silica gel, eluent ethyl acetate/methanol (v/v 2/1)/1% acetic acid. The pooled fractions are concentrated and precipitated from 10 ml of ethyl acetate/THF (v/v 1/1) using diisopropylether. The precipitation is removed by filtration and concentrated in a high vacuum over CaCl$_2$.

Yield: 230 mg (0.47 mmol) 35% of theoretical

TLC: Silica gel (Merck 60), ethyl acetate/methanol (v/v 2/1)/1% glacial acetic acid, detection with potassium permanganate $R_f$=0.63

$^1$H-NMR (D$_6$-DMSO/TMS): δ=1.14–1.50 (m, 12H, 6 C$\underline{H}_2$); 2.09 (t, 2H, C$\underline{H}_2$-CO, J=6.6 Hz); 2.22 (t, 2H, C$\underline{H}_2$-CO, J=7.5 Hz); 3.37 (m, 6H, C$\underline{H}_2$-N); 4.07 (m, 1H, C$\underline{H}$-N); 7.00 (s, 2H, C$\underline{H}$=); 7.85 ppm (m, 2H, N$\underline{H}$-CO).

1.5 N-α-(6-maleinimidohexanoyl)-ε-maleinimido-α-aminohexanoyl-β-alanyl-(N-hydroxysuccinimide) (α-MHS-ε-Mal-Lys-β-Ala-OSu)

180 mg (0.36 mmol) of the compound of example 1.4 are dissolved in 10 ml of absolute DMF, 49 mg (0.43 mmol) N-hydroxysuccinimide and 60 µl (0.43 mmol) morpholinoethyl isocyanate (MEI) added are and stirred for 16 hours at 20° C. Then 49 mg (0.43 mmol) N-hydroxysuccinimide and 60 µl (0.43 mmol) MEI were added twice, each time after 8 hours. To achieve a complete reaction, stirring was continued for another 6 hours. Subsequently, the solvent was removed in a high vacuum, the residue digested with 25 ml ethyl acetate, insoluble components removed by filtration and the filtrate concentrated to approximately 10 mi. The product dissolved in little ethyl acetate is added dropwise to 200 ml diisopropylether, the precipitated substance is removed, washed with diisopropylether and dried in a drying chamber with CaCl$_2$.

Yield: 115 mg (0.20 mmol) 56% of theoretical

TLC: Silica gel (Merck 60), ethyl acetate/methanol (v/v 2/1)/1% glacial acetic acid; detection with potassium permanganate $R_f$=0.83

$^1$H-NMR (D$_6$-DMSO/TMS): δ=1.06–1.50 (m, 12H, 6 C$\underline{H}_2$); 2.08 (t, 2H, C$\underline{H}_2$CO, J=6.7 Hz); 2.50 (t, 2H, C$\underline{H}_2$COOSu); 2.81 (s, 4H, 2 C$\underline{H}_2$COO); 3.31 (m, 6H, 3 C$\underline{H}_2$N); 4.12 (m, 1H, CH-NH); 6.98 (s, 4H, C$\underline{H}$=); 7.81 (d, 1H, N$\underline{H}$CH, I=7.0 Hz); 8.03 ppm (t, br, 1H, N$\underline{H}$CH$_2$).

EXAMPLE 2

2.1 N-α-Boc-ε-maleinimido-α-aminohexanoyl-DADOO-biotin (α-Boc-ε-Mal-Lys-DADOO-biotin)

While stirring, 422 mg (3.67 mmol) N-hydroxysuccinimide and 757 mg (3.67 mmol) dicyclohexylcarbodiimide are added to a solution of 1.00 g (3.06 mmol) of the compound prepared according to example 1.1 in 50 ml THF. After stirring for 1 hour, a solution of 1.37 g (3.67 mmol) biotin-DADOO in 50 ml of 0.1M KPO$_4$ buffer pH 8.5 is added dropwise at a temperature of 20° C. The mixture is stirred for another 2 hours at 20° C. Subsequently, the organic solvent is removed in a vacuum produced by a water pump and the aqueous phase is lyophilized. The raw product is purified by means of silica gel chromatography, eluent ethyl acetate/methanol (v/v 2/1)/1% acetic acid.

Yield: 930 mg (1.36 mmol) 44% of theoretical

TLC: Silica gel (Merck 60), ethyl acetate/methanol (v/v 2/1)/1% glacial acetic acid Detection with biotin spray and potassium permanganate $R_f$=0.44

$^1$H-NMR (D$_6$-DMSO/TMS): d=1.10–1.90 (m, 15H, $^t$Bu and 6 C$\underline{H}_2$); 2.06 (t, 2H, C$\underline{H}_2$CO, J=6.7 Hz); 2.60–2.90 (m, 3H, C$\underline{H}$S and CH$_2$S); 3.00–3.60 (m, 14H, 3 C$\underline{H}_2$N and 4 C$\underline{H}_2$O); 3.77 (m, 1H, C$\underline{H}$NH-Lys); 4.14 (dd, 1H, C$\underline{H}$-NH-biotin); 4.14 (dd, 1H, C$\underline{H}$-NH-biotin); 4.30 (dd, 1H, C$\underline{H}$NH-biotin); 4.30 (dd, 1H, C$\underline{H}$NH-biotin); 6.39 (m, 2H, N$\underline{H}$-biotin); 6.76 (d, 1H, N$\underline{H}$COO, J=7.1); 6.99 (s, 2H, C$\underline{H}$=); 7.84 ppm (t, br, 2H, 2 N$\underline{H}$CO).

2.2 ε-Maleinimido-a-aminohexanoyl-DADOO-biotin (ε-Mal-Lys-DADOO-biotin) 9

10 ml trifluoroacetic acid are added to 500 mg (0.7 mmol) of the compound prepared according to example 2.1 at 0° C. which is then slowly heated up to 20° C. After 30 min, the solution is diluted with 10 ml ethyl acetate and stirred for another 15 min. The solvent is removed in a vacuum produced by a water pump and the residue is dissolved in dioxane/water (v/v 1/1) and a lyophilisate is produced.

Yield: approx. 0.7 mmol

TLC: Silica gel (Merck 60), ethyl acetate/methanol (v/v 1/1)/1% glacial acetic acid Detection with biotin spray, potassium permanganate and ninhydrin $R_f$=0.08

2.3 N-α-maleinimidohexanoyl-ε-maleinimido-α-aminohexanoyl-DADOO-biotin (α-MHS-ε-MAL-Lys-DADOO-biotin, MALOS-biotin)

0.7 mmol of the compound prepared according to example 2.2 are dissolved in 10 ml of 0.1M KPO₄ buffer pH 7.5 to which then 260 mg maleinimidohexanoic acid-N-hydroxysuccinimide (MHS) in 10 ml THF are added. The pH value is then adjusted to pH 7.5 using 1N sodium hydroxide solution until the pH value no longer changes. After stirring for 16 hours at 20° C., the organic solvent is removed in a vacuum produced by a water pump and the residue is lyophilized. The raw product is purified with silica gel, eluent: ethyl acetate/methanol (v/v 1/1)/1% acetic acid. The pooled fractions are concentrated in a vacuum produced by a water pump, the residue dissolved in dioxane, insoluble components are removed by filtration, and the remaining portion is lyophilized.

Yield: 500 mg (still contains dioxane and acetic acid)

TLC: Silica gel (Merck 60), ethyl acetate/methanol (v/v 1/1)/1% glacial acetic acid Detection with biotin spray and potassium permanganate $R_f$=0.55

$^1$H-NMR (D₂O/TMS-Na-salt): d=1.20–1.80 (m, 18H, 9 C$\underline{H}_2$); 2.22 (m, 4H, 2 C$\underline{H}_2$CO); 2.71–2.90 (m, 3H, C$\underline{H}$S and C$\underline{H}_2$S); 3.38–3.75 (m, 16H, 4 C$\underline{H}_2$N and 4 C$\underline{H}_2$O); 4.20 (m, 1H, C$\underline{H}$NH-Lys); 4.44 (dd, 1H, C$\underline{H}$NH-biotin); 4.60 (dd, 1H, C$\underline{H}$NH-biotin); 6.88 ppm (s, 4H, C$\underline{H}$=).

EXAMPLE 3

Activation of proteins with linkers of the invention.

3.1 Activating KLH 150 mg (5×10⁻⁵ mmol/l) Keyhole Limpet Hemocyanin (KLH) are dissolved in 5 ml of 0.1 mol/l potassium phosphate/0.05 mol/l sodium chloride buffer, pH 8.5, and with 5×10⁻² mmol/l of linker according to the invention (example 1.5) added to 2.5 ml dioxane. After stirring for 60 minutes at 20° C., the pH value is adjusted to 8.5 using 0.1 mol/l sodium hydroxide solution and stirring is continued for another 3 hours at 20° C. The mixture is purified by means of gel chromatography using an ACA 202 column 40×3 cm, eluent: 0.1 mol/l potassium phosphate/0.05 mol/l sodium chloride buffer, pH 7.0).

3.2 Activating POD with linkers of the invention

The activation is carried out in a molar excess of linker (example 1.5) to POD of 25:1.

POD at a concentration of 25 mg/ml is dissolved in 50 mM potassium phosphate buffer pH 7.5, 150 mM NaCl. The corresponding amount of linker is prediluted in DMSO using 100 mg/ml. 92 μl/ml POD of this solution are added to the POD solution. The pH of the mixture is checked and adjusted to 7.0. Subsequently, the mixture is incubated for 1 hour at 25° C. under stirring. The reaction is terminated by changing the pH to 6.1 and cooling the mixture in an ice-bath. Subsequently, non-coupled linker is separated by means of flow dialysis against 10 mM potassium phosphate buffer, pH 6.1, 50 mM NaCl, 1 mM EDTA. The incorporation of the MH groups is determined in a reaction with a defined amount of cystein and titration of the residual amount of cystein with dithiodipyridin.

EXAMPLE 4

4.1 Bis(3-phthalimidopropyl)malonic Acid Dimethylester 1.14 ml (10 mmol) of malonic acid dimethylester and 8.04 g (30 mmol) of n-(3-bromopropyl)phthalimide are dissolved in 50 ml absolute tetrahydrofurane in a nitrogen atmosphere. At 25° C., 0.24 g (10 mmol) of sodium hydride are added. The mixture was refluxed and heated for 8–10 hours. After cooling, another 0.24 g (10 mmol) sodium hydride were added and again refluxed and heated for 20–72 hours. Subsequently, the solvent was removed by distilling in a vacuum produced by a water pump. Then the residue was suspended with 200 ml ethyl acetate and the two-phase suspension was washed with 50 ml of water. The aqueous phase was separated and the remaining suspension was filtered. The main portion of the product was recovered from the filter cake by recrystallization in acetone. The filtrate was concentrated until dry in a vacuum produced by a water pump. Another product was obtained by recrystallization in acetone.

Yield: 2.78 mg (5.5 mmol) 55% of theoretical

TLC: Silica gel (Merck 60), ethyl acetate/hexane (v/v ½) Detection with UV absorption
$R_f$=0.55 N-(3-bromopropyl)phthalimide
$R_f$=0.44 (3-phthalimidopropyl) malonic acid dimethylester
$R_f$=0.32 bis-(3-phthalimidopropyl) malonic acid dimethylester

4.2 5-amino-2-(3-aminopropyl)pentanoic Acid 1.0 g (2 mmol) of bis-(3-phthalimidopropyl)malonic acid dimethylester from example 4.1 are dissolved in 40 ml methanol and stirred with 10 ml of a 20% methanolic KOH (w/v) for 15 hours at room temperature. Then the acidity is increased by adding 6N hydrochloric acid, precipitated potassium chloride is separated and the solvent is removed by distilling in a vacuum produced by a water pump. The residue is suspended in 2 ml mesitylene and 5 ml glacial acetic acid and heated under reflux for 12 hours. The solvent is removed by distilling in a high vacuum, the residue is dried for 16 hours in the exsiccator using potassium hydroxide. The raw product is dissolved in 10 ml methanol and heated under reflux for several days with 5 ml hydrazine hydrate. The solvent and excess hydrazine hydrate are removed by distilling in a high vacuum, the residue is dissolved several times in methanol and again concentrated in a high vacuum. Then, the mixture is dispersed in 1N hydrochloric acid and non-dissolved products are removed by filtration. The product is recovered from the mother lye by means of cation exchange chromatography (Dowex 50×2–200) (salt elution with water, product elution with 1N –5N ammonium).

Yield: 191 mg (1.1 mol)55 of theoretical

TLC: Silica gel 60, water/s-butanol/glacial acetic acid/ethyl acetate (v/v/v/v 1/1/1/1)

$R_f$=0.14 5 amino-2-(3-aminopropyl)pentanoic acid $^1$H-NMR (D$_6$-DMSO/TMS): δ=1.37 (m, 8H, 4C$\underline{H}_2$); 2.22 (m, 1H, C$\underline{H}$-COO); 2.72 (m, 4H, 2C$\underline{H}_2$-N); 8.07 ppm (m, 6H, 2 N$^+\underline{H}_3$).

4.3
5-N-maleinimido-2-(3-N-maleinimidopropyl)pentanoic Acid 620 mg (4 mmol) methoxycarbonylmaleinimide are added to 420 mg (2 mmol) of 5-amino-2-(3-aminopropyl)pentanoic acid hydrochloride from example 4.2 in 15 ml saturated sodium hydrogen carbonate solution and stirred while cooled in ice. After 3 hours, another 350 mg (2.25 mmol) of methoxycarbonylmaleinimide are added and stirred for another 2 hours while cooled on ice. Subsequently, a pH of 4–5 is adjusted using 2M hydrochloric acid and the mixture is lyophilized. The lyophilisate is purified via preparative HPLC (column: Waters Delta-PAK™, C18, 50×300 mm, 300 Å, 15 µ, eluent A: 0.01% TFA, eluent B: acetonitrile with 0.01 TFA, gradient: 0% B according to 100% B, detection at 226 nm).

Yield: 216 mg (0.65 mmol) 33% of theoretical

TLC: Silica gel (Merck 60), n-butanol/glacial acetic acid/water (v/v/v 3/1/1), Detection with potassium permanganate spray $R_f$=0.16 5-amino-2-(3-aminopropyl)pentanoic acid)

$R_f$=0.71  5-N-maleinimido-2-(3-N-maleinimidopropyl)pentanoic acid

Analytic HPLC:

Column: Vydac C18, 4.6×250 mm, 5 µ, 300 Å

Eluent: A: Millipore water, 0.01% TFA B: Acetonitrile, 0.01% TFA

Flow: 1 ml/min

Gradient: 0→50% B in 45 min

Detection: 226 nm

Retention times: t=33.3 min 5-N-maleinimido-2-(3-N-maleinimidopropyl)-pentanoic acid $^1$H-NMR (D$_6$-DMSOFFMS): δ=1.51 (m, 8H, 4C$\underline{H}_2$); 2.27 (m, 1H, C$\underline{H}$-COO); 3.48 (t, J=6.7 Hz, 4H, 2 C$\underline{H}_2$-N); 6.91 ppm (s, 4H, 2 C$\underline{H}$=C$\underline{H}$).

4.4
5-N-maleinimido-2-(3-N-maleinimidopropyl)pentanoic acid-N-hydroxysuccinimide 200 mg (0.65 mmol) 5-N-maleinimido-2-(3-N-maleinimidopropyl)pentanoic acid are dissolved in 5 ml tetrahydrofurane to which 88.6 mg (0.77 mmol) N-hydroxysuccinimide and 159 mg (0.77 mmol) dicyclohexylcarbodiimide are added. The mixture is stirred for 10 hours at 25° C. Then, 50 µl of acetic acid are added to the suspension and the mixture is again stirred for 1 hour and then filtered via suction filter. The separated urea is quickly rinsed with 1 ml ethyl acetate, the flitrate is concentrated and purified via preparative HPLC (conditions see example 4.3) and then immediately lyophilized.

Yield: 150 mg (0.35 mmol) 54% of theoretical

Analytic HPLC:

Column: Vydac C18, 4.6×250 mm, 5 µ, 300 Å

Eluent: A: Millipore water, 0.01% TFA B: Acetonitrile, 0.01% TFA

Flow: 1 ml/min

Gradient: 0→50% B in 45 min

Detection: 226 nm

Retention times:

t=33.3 min  5-N-maleinimido-2-(3-N-maleinimidopropyl)-pentanoic acid t=39.0 min  5-N-maleinimido-2-(3-N-maleinimidopropyl)-pentanoic acid-N-hydroxysuccinimide Conjugates using the linker of the present invention are disclosed in German Patent Application P 43 10 142.9 and the corresponding U.S. application filed of even date herewith entitled "Immunologically Active Conjugates and Method for their Preparation (Attorney Docket P1614-4012). The entire disclosure of such copending application is hereby incorporated by reference for such teachings therein.

We claim:

1. Compound of the formula

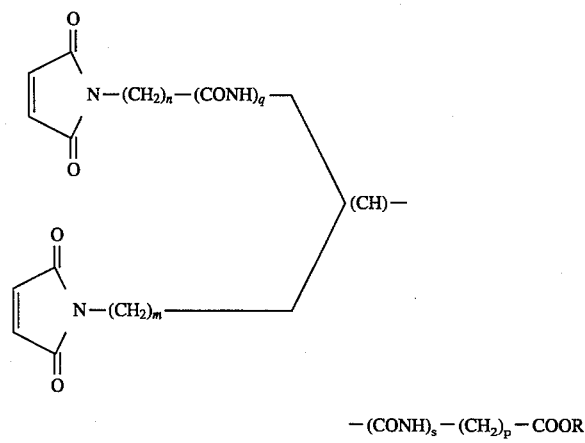

wherein

R is an ester-activating group selected from the group consisting of a N-hydroxyester group, an imidazolide, a pyridazolide, an aminoalkyl carboxylic acid and an activated arylester group;

m and n are the same or different and are 0–6;

q and s are 0 or 1; and p is o when s is 0, and p is 2–4 when s is 1.

2. Compound of claim 1, wherein R is hydroxysuccinimidyl.

3. Compound of claim 2, wherein n and m are each 4; and p, q and s are each 0.

4. Compound of claim 2 wherein n and m are each 5; and p, q and s are each 0.

5. Compound of claim 2, wherein n and m are each 3; and p, q and s are each 0.

6. Compound of claim 2, wherein n is 5;

m is 4;

q is 1; and p and s are each 0.

7. Compound of claim 2, wherein n is 5;

m is 4;
p is 2; and
q and s are each 1.

8. A method of preparing a compound of the formula

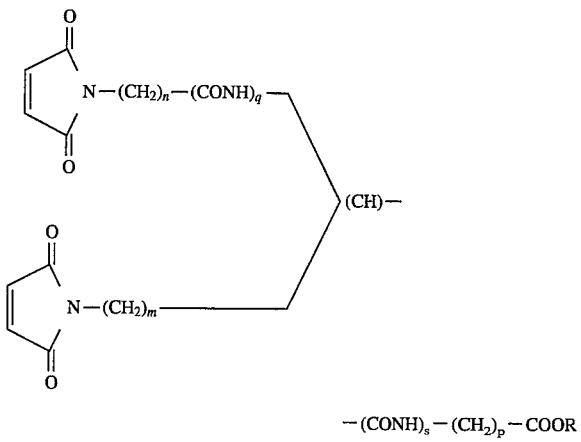

wherein R is an ester-activating group;
m and n are the same or different and are 0–6;
p and s are each 0; and
q is 0
comprising
- a) forming a dialkylmalonic acid diester by a two-fold malonic ester synthesis from N-phthalimidoalkylhalogenide and a malonic acid diester
- b) ester cleaving the dialkyl malonic acid diester under acidic conditions and decarboxylating the cleaved product;
- c) hydrolyzing the decarboxylated product under acidic conditions to release amino groups from the N-phthalimidoalkyl groups;
- d) treating the hydrolyzed product with alkoxy-carbonyl-maleininimide to incorporate maleinimido residues; and
- e) activating the carboxyl groups to form an activated ester.

* * * * *